United States Patent [19]

Servas

[11] Patent Number: 5,322,062
[45] Date of Patent: Jun. 21, 1994

[54] NON-INFLATABLE SEALING CUFF FOR TRACHEAL TUBE AND OTHER CANNULA

[76] Inventor: Francis M. Servas, 31882 Paseo Labranza, San Juan Capistrano, Calif. 92675

[21] Appl. No.: 44,957
[22] Filed: Apr. 8, 1993
[51] Int. Cl.⁵ .............................................. A61M 16/00
[52] U.S. Cl. .............................. 128/207.14; 128/207.15
[58] Field of Search ...................... 128/207.14, 207.15, 128/200.26; 604/268, 278, 279, 280

[56] References Cited

U.S. PATENT DOCUMENTS

| 724,913 | 4/1903 | Montgomery | 604/278 |
|---|---|---|---|
| 1,383,502 | 7/1921 | Vultee | 604/279 |
| 3,516,410 | 6/1970 | Hakim | 604/268 |
| 3,659,611 | 5/1972 | Miller | 128/207.15 |
| 3,810,474 | 5/1974 | Cross | 128/207.15 |
| 4,018,231 | 4/1977 | Wallace | 128/207.15 |
| 4,340,046 | 7/1982 | Cox | 128/207.15 |

Primary Examiner—Edgar S. Burr
Assistant Examiner—Aaron J. Lewis
Attorney, Agent, or Firm—Roger C. Turner

[57] ABSTRACT

The present invention discloses a sealing cuff for an elongated tubular cannula, for forming an adequate fluid seal between the cannula and a body passageway when the cannula is inserted into the passageway. The sealing cuff comprises a plurality of thin flexible resilient annular slit discs extending generally perpendicularly from the cannula with a rim having a diameter larger than the opening of the body passageway. The slit discs haves a series of slits extending generally radially outwardly to the rim, dividing the disc into annular sectors, so that when the cannula is inserted into the body passageway, each sector can independently bend, overlap and readily conform to the wall of the passageway. The sealing cuff further comprises a plurality of thin flexible resilient annular solid discs extending generally perpendicularly from the cannula and having a diameter smaller than that of the body passageway, and arranged alternately between said slit discs. The discs of the sealing cuff for use on a tracheal tube can be "D-shaped" to facilitate conforming to the shape of the trachea.

15 Claims, 3 Drawing Sheets

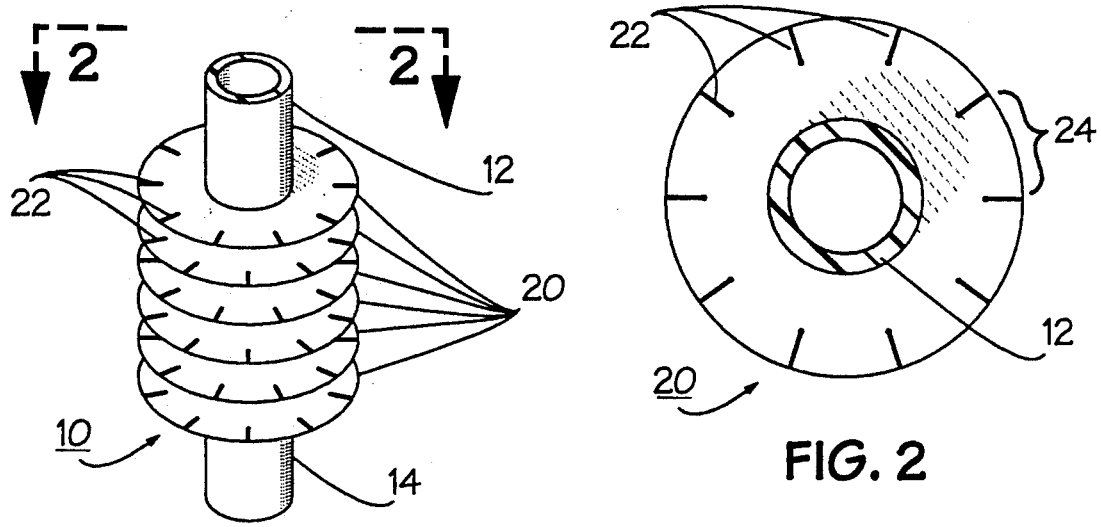
FIG. 1
FIG. 2
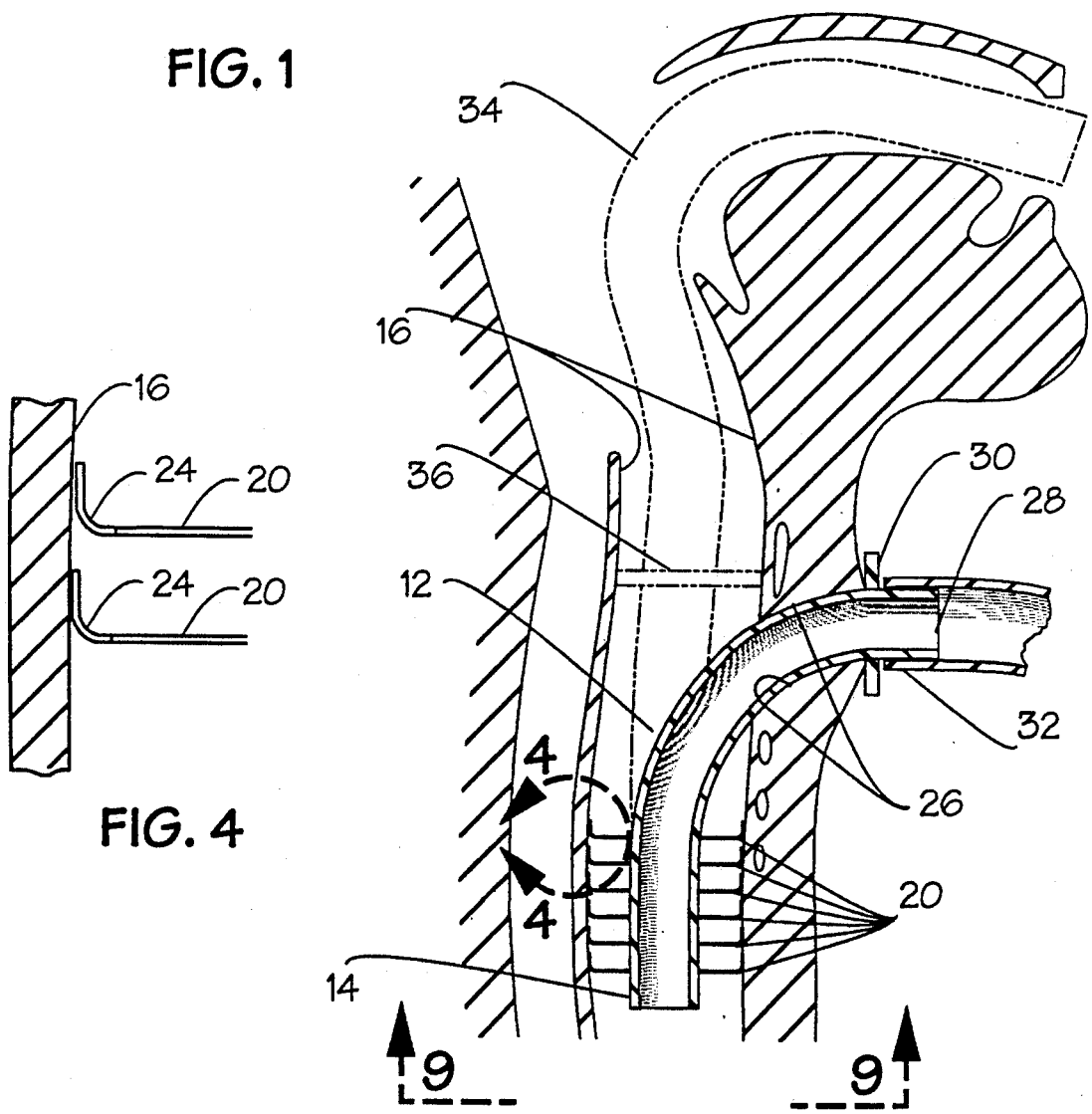
FIG. 4
FIG. 3

NON-INFLATABLE SEALING CUFF FOR TRACHEAL TUBE AND OTHER CANNULA

BACKGROUND OF THE INVENTION

The present invention relates to medical catheters and cannula, and more particularly to tracheal tubes.

Tracheal tubes have been used for some time to administer anesthesia to a patient, and to provide a bypass supply of air or mixture of gases to a patient having an obstruction in the upper area of the throat. Tracheal tubes can be in the form of a long flexible endotracheal tube wherein the distal end can be inserted into the trachea through the nose or mouth of the patient, or can be a short curved tracheostomy tube wherein the distal end can be inserted into the trachea through a surgical incision in the neck of the patient. The proximal end of the tracheal tube remains outside the trachea in communication with ambient air to permit passage of such air into the trachea.

The proximal end of the tracheal tube can also be attached to a respiratory device to assist the patient's breathing. The distal end typically includes an inflatable cuff as described in U.S. Pat. No. 3,659,612 which is inflated after the tube is positioned to provide a fluid seal between the distal end of the tube and the wall of the trachea. The inflatable cuff includes a thin film elastic balloon which is bonded around the tube, having an inflation line extending from the balloon to the proximal end of the tube, and can further include check valves, relief valves, and external bulb indicators to help maintain the desired pressure within the cuff. Excessive pressure in the cuff can cause severe damage to the wall of the trachea, and insufficient pressure can result in an inadequate seal. When the inflatable cuff is properly designed, manufactured, handled, and used, it performs a safe and effective fluid seal. A problem with the inflatable cuff is that the cuff and inflation line are costly and difficult to manufacture. Another problem is that the inflatable cuff is very delicate and easily damaged during handling and in use; any leak in the balloon, inflation line or check valve will allow the cuff to collapse and not provide an adequate seal.

U.S. Pat. No. 3,659,611 discloses an early non-inflatable tracheal tube seal, in which the distal end of the device includes a series of three resilient, solid disc, silicon flanges to engage the wall of the trachea. An apparent problem with the solid disc flanges is that the discs must be larger than the trachea to insure an occluding seal, but the oversized discs cannot conform to a smaller opening without bending and buckling around the periphery of the disc. The bending and buckling around the periphery of the discs can result in an ineffective seal, and can result in stress concentrations which may produce excessive localized pressure on the tracheal wall.

Other medical procedures often require placement and sealing of a small cannula or catheter within a body passageway, for example an arterial or venous catheter within a blood vessel. Such cannula may be difficult to seal and can require a "cut down" surgical procedure of the vessel, with clamps and sutures to adequately seal the cannula within the body passageway.

It is a object of the present invention to provide a safe, effective, reliable and durable fluid sealing cuff between a cannula and a body passageway.

It is another object to provide a non-inflatable sealing cuff for a tracheal tube which is not difficult and not expensive to manufacture; and safe, effective, reliable and durable in use.

SUMMARY OF THE INVENTION

The foregoing objects are accomplished by a sealing cuff for an elongated tubular cannula, for forming an adequate fluid seal between the cannula and a body passageway when the cannula is inserted into the passageway. The sealing cuff comprises a plurality of thin flexible resilient annular discs extending generally perpendicularly from the cannula with a rim having a diameter larger than the opening of the body passageway. The discs have a series of slits extending generally radially outwardly to the rim, dividing the rim into annular sectors, so that when the cannula is inserted into a body passageway, each sector can independently bend, overlap and readily conform to the wall of the passageway.

Another embodiment of the sealing cuff further comprises a plurality of thin flexible resilient annular solid discs extending generally perpendicularly from the cannula and having a diameter smaller than that of the body passageway, and arranged alternately between said slit discs.

The sealing cuff is particularly useful to seal tracheal tubes with the trachea of a patient. Another embodiment includes the discs having a D-shape to facilitate conforming to the shape of the trachea of a patient.

BRIEF DESCRIPTION OF THE DRAWINGS

While the novel features of the invention are set forth in the appended claims, the invention will be better understood along with other features thereof from the following detailed description taken in conjunction with the drawings in which:

FIG. 1 is a front perspective view of the distal end of a tracheal tube illustrating one embodiment of the present invention;

FIG. 2 is a sectional view taken along 2—2 of FIG. 1, which is slightly enlarged;

FIG. 3 is a side elevational sectional view of a tracheostomy tube incorporating the present invention, inserted into the trachea of a patient;

FIG. 4 is an enlarged detail view of the inscribed area 4—4 of FIG. 3;

DETAILED DESCRIPTION OF THE INVENTION

Figure 5:
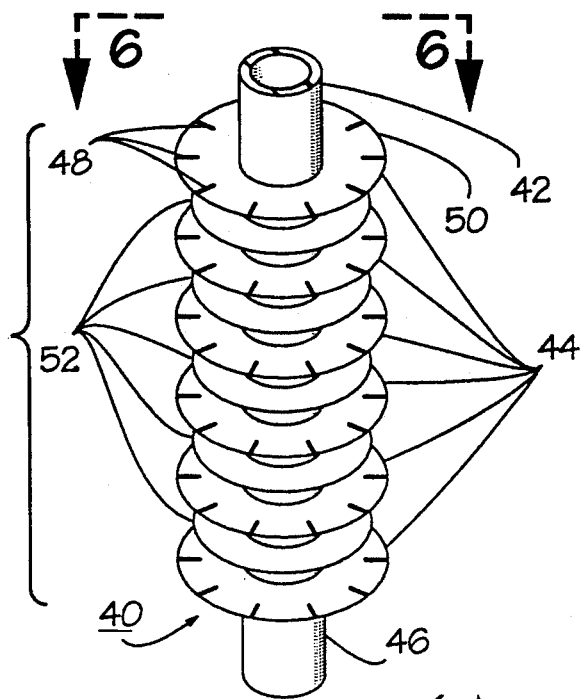
FIG. 5 is an exploded front prospective view illustrating another embodiment of the present invention.
Figure 6:
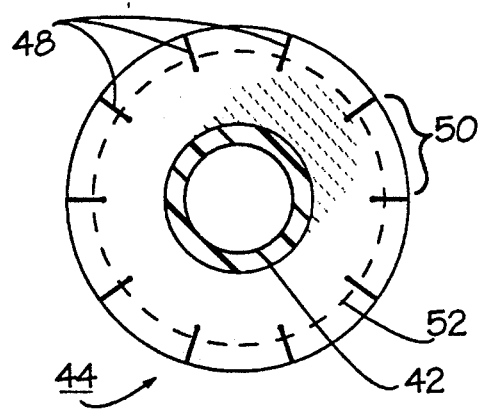
FIG. 6 is a plan view of FIG. 5 which is slightly enlarged.
Figure 8:
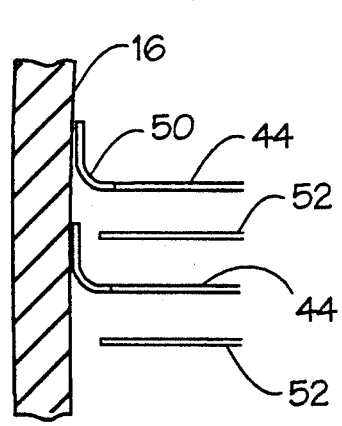
FIG. 8 is an enlarged detail view of the inscribed area 8—8 of FIG. 7.
Figure 7:
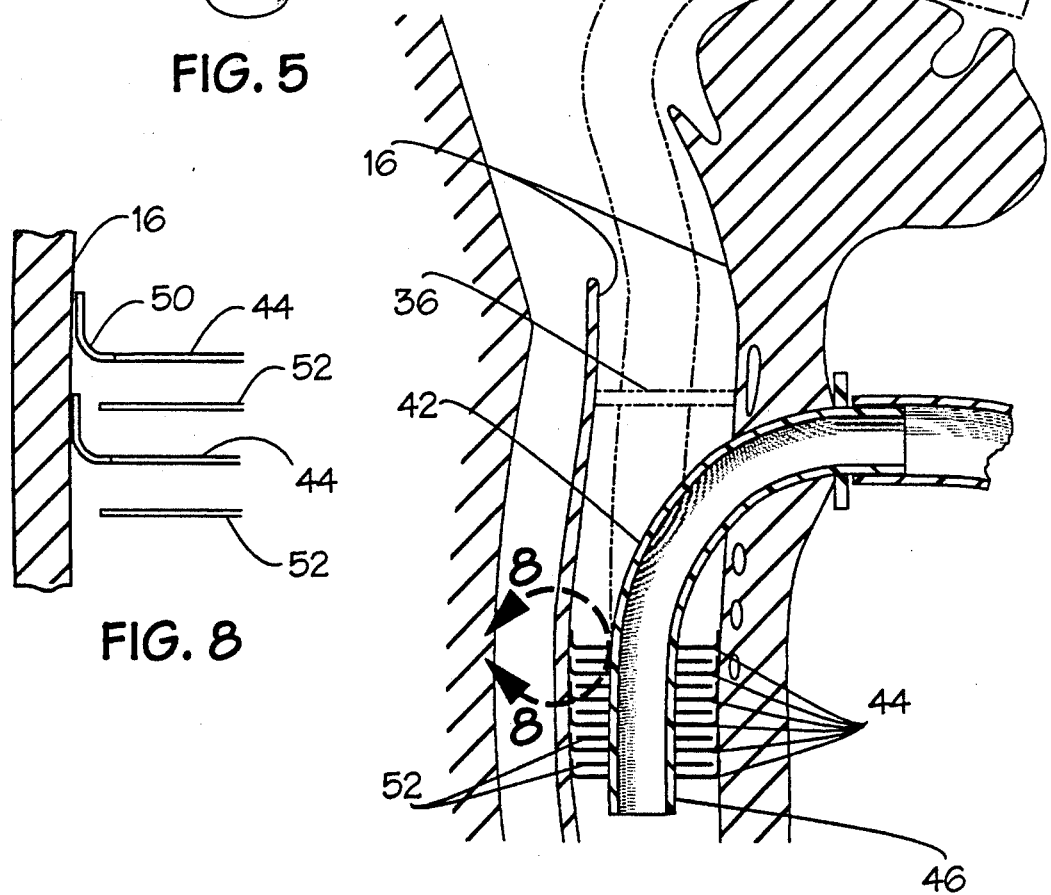
FIG. 7 is a side elevational sectional view of a tracheostomy tube incorporating the second embodiment of the invention, inserted into the trachea of a patient.

Referring first to FIGS. 1, 2 and 3, there is illustrated an example of a first embodiment of the present invention, as a sealing cuff 10 formed on the tubular cannula 12 of a tracheal tube. The tubular cannula has a distal end 14 which is to be inserted within the trachea 16 of a patient, and the sealing cuff is to provide an adequate fluid seal between the cannula and the wall of the trachea.

The sealing cuff 10 comprises a plurality of slit sealing discs 20. The sealing discs are thin flexible resilient annular discs which extend generally perpendicularly from the distal end 14 of the cannula. The discs have a diameter larger than the opening of the trachea, and can be sized correspondingly with the various sizes of tracheal tubes. An example of a typical size of the disc is about 1.25 inch in diameter.

A unique feature of the sealing disc 20 is a series of slits 22 which extend generally radially outwardly to the rim of the disc. The slits in the disc function to substantially improve the flexibility and conformability of the rim of the disc upon engagement with the wall of the trachea. As previously discussed, the diameter of such disc must be larger than the opening to be sealed; and upon engagement of a "solid" (prior art) disc within the smaller opening can result in wrinkling and buckling-of the rim and surface of the solid disc, which can preclude the desired seal and can create stress concentrations on the wall of the trachea. In addition, the shape of the trachea at the distal end of the positioned cannula is not usually round and can vary from oval to "D-shaped" (see FIG.9), and it can be quite difficult for a solid disc to conform and seal around such irregular shapes. The slits of the present invention divide the disc into annular sectors 24 in which the tips of each sector can independently bend, twist, and overlap with adjacent sectors, if necessary, to conform to the wall of the trachea.

The number, spacing and length of the slits 22 are each variable to produce the desired flexibility, conformability, rigidity, seal pressure and durability of the discs of the sealing cuff. For some design applications, it may be desirable to have the slits extend from the base of the cannula 12 to the rim of the discs, with numerous tightly spaced sectors, for maximum flexibility (but which may be allow some fluid flow leakage through the slits). Other material thicknesses and selections may dictate slits which emanate from points between the cannula and the rim, for improved sealing features with perhaps fewer discs. The present embodiment of sealing cuff 10 provides adequate flexibility and fluid seal with about six to ten discs 20 formed of 0.003 inch thin silicon (or polyurethane, flexible polyvinylchloride or like polymer) having slits 22 extending about 0.1 inch, about every thirty-six degrees, forming about ten sectors 22, with each disc spaced adjacently about 0.1 inch apart on the distal end of the cannula.

The slits 22 of the disc may be fabricated by shearing a "flush" slit between sectors, or can be a "clearance" slit (or a slot) having a few degrees, or a few thousands of an inch, of clearance between sectors. The clearance permits the sectors to be even more flexible, and can permit the tips of the sectors to conform to smaller shapes without overlapping, which can provide a better seal in certain applications. The slits can also be fabricated so that the slits extend from emanation points shaped as small apertures to facilitate flexibility of the sectors, and which terminates the slit and prevents the slits from tearing inwardly toward the cannula.

It may be advantageous to arrange the discs 20 so that the slits 22 of adjacent discs are not in alignment. Such an arrangement will avoid direct leakage paths between adjacent discs, and even if there is some leakage between the slits, the leakage flow must meander between discs which would provide resistance to the leakage and result in a better seal.

Referring particularly to FIG.3 and also to FIG.4, the tracheal tube with the sealing cuff 10 is shown positioned within the trachea 16 of a patient. The cannula 12 of the tracheal tube is shown as a tracheostomy tube of which the distal end 14 has been inserted into a stoma 26 created in the neck of the patient, and the proximal end 28 has been secured by a suitable neck flange 30 tied by a strap around the neck of the patient. The proximal end 28 is further attached to a respirator device 32 to facilitate breathing of the patient. The dashed lines 34 illustrate the analogy of cannula 12 as an elongated endotracheal tube of which the distal end 14 and sealing cuff 10 is inserted into the mouth and through the larynx 36 of a patient and similarly positioned within the trachea.

Upon the initial insertion of the distal end 14 through the stoma 24 (or through the larynx 36), the flexible sealing discs 20 are naturally collapsed and compressed by the stoma until the distal end passes into the trachea; the resilient discs 20 then progressively return to their extended generally perpendicular configuration; however, the tips of sectors 24 of the split discs now engage and readily conform to the wall of the trachea 16 to provide an adequate sealing cuff around the cannula.

The sealing cuff 10 as utilized on tracheal tubes does not require an absolute air-tight or liquid-tight seal of each disc with the tracheal wall. Respiration devices operate at a relatively low pressure of about 25 to 50 millimeters of mercury, to apply air and oxygen to the lungs of the patient. The sealing cuff 10 acts as a resistance occluder to any bypass flow around the distal end of the cannula, and the respirator gas follows the path of least resistance into the lungs. In some applications, only one or a few slit disc 20 may be sufficient to provide a barrier to bypass flow and to provide an adequate seal.

Referring now to FIGS. 5, 6, 7 and 8 there is illustrated an example of another embodiment of the present invention as a sealing cuff 40 formed on the tubular cannula 42 of a tracheal tube. The sealing cuff 40 comprises a plurality of thin, flexible, resilient slit annular discs 44, extending generally perpendicularly from the distal end 46 of the cannula. The slit discs 44 include a series of unique slits 48 which extend generally radially outwardly to the rim of the disc, and divide the disc into annular sectors 50. The slit discs 40 with sectors 50 are similar in design and function, to the slit discs (20) discussed in reference to FIG.1. and are similarly spaced apart along the distal end of the cannula. The sealing cuff 40 further comprises a plurality of thin flexible resilient annular solid discs 52 extending generally perpendicularly from the distal end of the cannula. Each of the solid discs 52 are arranged adjacently to a slit disc 44 and spaced apart along the distal end of the cannula.

The solid discs 52 greatly compliment the function of the slit disc 44 to provide an even more adequate and effective seal with the trachea. The solid discs can have a diameter similar to that of the slit disc to seal against the wall of the trachea in the traditional manner. However, it is preferable that the diameter of the solid disc be smaller than the diameter of the slit disc, and even smaller than the opening of the passageway to be occluded. The reduced diameter solid discs have limited engagement with the wall of the trachea, and therefore are not usually wrinkled or buckled, and retain their perpendicular orientation between the slit discs. The slits discs flex, bend and conform to the contour of the wall of the trachea and reliably block and prevent any leakage paths around the sealing cuff, but the slits 48 can sometimes permit leak paths through the slit discs of the sealing cuff; while the solid discs may allow leakage around the discs but reliably block and prevent any leak paths through the body of the sealing cuff. The combination of the alternate slit disc and solid disc provides a labyrinth path for any leakage to alternately travel through a slit disc, then around a solid disc throughout the sealing cuff to therefore provide an excellent barrier to bypass flow and an adequate seal with the trachea. The solid discs also tend to support and align any slit discs that may become misaligned during handling or during installation of the tube.

The selection of the thickness, diameters, materials, slit depth and pattern of the slit discs; and the thickness, materials, and the diameter of the solid discs; plus the relative spacing, orientation and arrangement of the discs along the cannula can each be varied in numerous combinations to provide an adequate seal of almost any cannula within any body passageway.

It was found that an excellent seal was provided on a tracheal tube utilizing about six slit discs 44 of 0.003 inch thin silicon having a diameter of about 1.25 inches, with each disc having slits of about 0.1 inch arranged about every 36 degrees dividing the disc into about ten sectors; and utilizing about five solid discs 52 having a diameter of about 1.0 inch with the solid discs arranged alternately between the slit discs and spaced adjacently about 0.1 inch apart along the distal end of the cannula.

Figure 9:
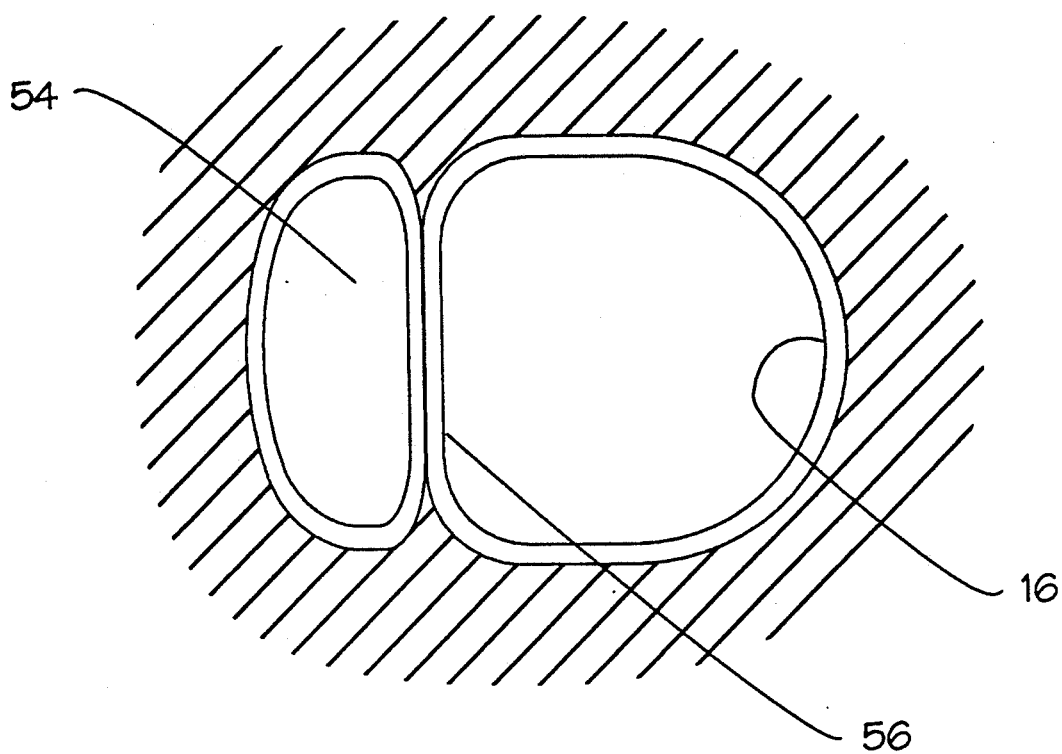
FIG. 9 is a sectional view taken along 9—9 of FIG. 3 which is slightly enlarged to illustrate the trachea and esophagus.
Figure 10:
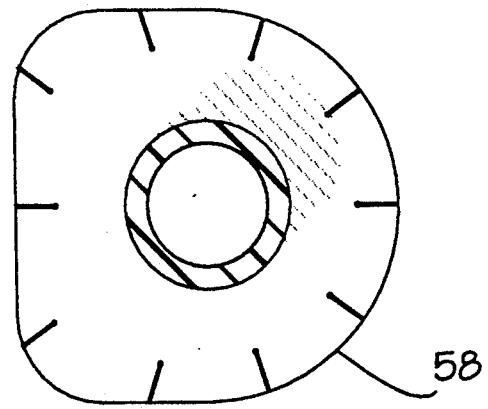
FIG. 10 is a plan view of a third embodiment of the present invention.

Referring now to FIGS. 9 and 10, there is shown a cross section of the trachea 16, also showing the esophagus 54 separated by the tracheal membrane 56 to illustrate the typical "D-shaped" tracheal opening. FIG. 10 illustrates a third embodiment of a sealing cuff having a sealing disc 58 specifically designed to conform to the D-shaped opening of the trachea, and is otherwise similar to the slit disc and solid disc components as described in reference to FIGS. 5,6,7, and 8.

While specific embodiments and examples of the present invention have been illustrated and described herein, it is realized that modifications and changes will occur to those skilled in the art. It is therefore to be understood that the appended claims are intended to cover all such modifications and changes as fall within the spirit and scope of the invention.

For example, the sealing discs of the present invention are described as extending "generally perpendicularly" from the cannula. In some applications of the sealing cuff, some or all of the discs may be fabricated having an angled or conical configuration; perhaps to facilitate insertion, or perhaps with a reverse angle conical configuration so that any bypass flow would tend to increase the engagement force of the sealing discs against the passageway for an improved seal. The term generally perpendicularly shall apply to such angled and conical configurations of the discs. Similarly, the term "generally radially" outwardly shall apply to slits which may be oriented at an angle or spiral or other such path to the rim of the discs. The term "discs" shall apply to discs which are circular, oval, D-shaped or customized in shape to fit a specific contour or body passageway; and shall apply to discs which are flat, tapered, or corrugated for a specific application.

What is claimed:

1. A sealing cuff on an elongated tubular cannula, for forming an adequate fluid seal between the cannula and a body passageway when the cannula is positioned in the passageway, comprising:
    at least one thin flexible resilient annular disc extending generally perpendicularly from the cannula with a rim having a diameter larger than the opening of the body passageway;
    said disc having a series of partial slits extending from points on the disc generally radially outwardly to the rim, dividing a portion of said disc into annular sectors, so that when the cannula is positioned in the body passageway, the rim of each sector can independently bend, overlap and readily conform to the wall of the passageway, while the body of said disc remains substantially planer.

2. The sealing cuff as in claim 1, wherein said slits extend from points about midway between the cannula and the rim of said disc.

3. The sealing cuff as in claim 2 comprising a plurality of at last three said slit discs which are spaced adjacently apart along the cannula.

4. The sealing cuff as in claim 3, further comprising at lest one thin flexible resilient annular solid disc extending perpendicularly from the cannula and having a diameter smaller than that of the body passageway, and arranged adjacently to at least one of said slit discs.

5. The sealing cuff as in claim 3, further comprising a plurality of thin flexible resilient annular solid discs extending perpendicularly from the cannula and having a diameter smaller than that of the body passageway, and arranged alternately between said slit discs.

6. The sealing cuff as in claim 3 wherein said discs are arranged so that the slits of adjacent discs are not in alignment.

7. A non-inflatable sealing cuff on a tracheal tube having an elongated tubular cannular with a distal end, for forming an adequate fluid seal between the distal end of the cannular and the wall of the trachea when the trachael tube is positioned in the trachea, comprising:
    at least one thin flexible resilient annular disc extending perpendicularly from the distal end of the cannula with a rim having a diameter larger than the opening of the trachea;
    said disc having a series of partial slits extending from points on the disc generally radially outwardly to the rim, dividing a portion of said disc into annular sectors, so that when the cannula is positioned in the trachea, the rim of each sector can independently bend, overlap and readily conform to the wall of the trachea, while the body of said disc remains substantially planer.

8. The sealing cuff as in claim 7, wherein said slits extend from points about midway between the cannula and the rim of said disc.

9. The sealing cuff as in claim 8 comprising a plurality of at least three said slit discs which are spaced adjacently apart along the cannula.

10. The sealing cuff as in claim 9 wherein said discs are arranged so that the slits of adjacent discs are not in alignment.

11. The sealing cuff as in claim 9, further comprising at least one thin flexible resilient annular solid disc extending perpendicularly from the cannula and having a diameter smaller than that of the trachea, and arranged adjacent to at least one of said slit discs.

12. The sealing cuff as in claim 11, comprising about six said slit discs having a diameter of about 1.25 inch, with each disc having slits of about 0.1 inch about every 36 degrees dividing each slit disc into about ten annular sectors, and further comprising about five said solid discs having a diameter of about 1.0 inch, with said solid discs arranged alternately between said slit discs, and said discs spaced about 0.1 inch apart on the distal end of the cannula.

13. The sealing cuff as in claim 11 wherein said discs are D-shaped to facilitate forming a seal with the trachea of a patient.

14. The sealing cuff as in claim 9 wherein said discs are D-shaped to facilitate forming a seal with the trachea of a patient.

15. The sealing cuff as in claim 9, comprising about ten said slit discs having a diameter of about 1.0 inch, with each disc having slits of about 0.1 inch about every 36 degrees dividing each disc into about ten annular sectors, with said slit discs spaced about 0.1 inch apart on the distal end of the cannula.

* * * * *